US008347551B2

(12) United States Patent
Van Der Drift

(10) Patent No.: US 8,347,551 B2
(45) Date of Patent: Jan. 8, 2013

(54) METHOD OF APPLYING PESTICIDES

(75) Inventor: Eric Van Der Drift, Enkhuizen (NL)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 11/569,754

(22) PCT Filed: Jun. 9, 2005

(86) PCT No.: PCT/EP2005/006208
§ 371 (c)(1),
(2), (4) Date: Nov. 29, 2006

(87) PCT Pub. No.: WO2005/120226
PCT Pub. Date: Dec. 22, 2005

(65) Prior Publication Data
US 2007/0249498 A1    Oct. 25, 2007

(30) Foreign Application Priority Data
Jun. 10, 2004   (GB) .................................. 0412974.8

(51) Int. Cl.
A01C 1/06        (2006.01)
A01N 25/26       (2006.01)
(52) U.S. Cl. ......................................... 47/57.6; 504/100
(58) Field of Classification Search ................... 47/57.6; 504/100
See application file for complete search history.

(56) References Cited

U.S. PATENT DOCUMENTS 3,156,550 A * 11/1964 Ernst-August ................ 504/189
4,272,920 A *  6/1981 Dawson ..................... 47/58.1 R
7,003,914 B2 *  2/2006 Legro et al. ............... 47/58.1 SE
2002/0129406 A1 *  9/2002 Asrar et al. ................... 800/295
2003/0224936 A1 * 12/2003 Kretzschmar ................ 504/100

FOREIGN PATENT DOCUMENTS

DE      3150631 A1       7/1983
WO       0113722 A        3/2001
WO    WO 01/13722    *    3/2001

OTHER PUBLICATIONS

Torres et al. "Relative effects of the insecticide thiamethoxam on the predator Podisus nigrispinus and the tobacco whitefly Bemisia tabaci in nectaried and nectariless cotton," Pest. Manag. Sci., Mar. 2003, 59(3), abstract only.*
Changchow Dist Inst Agric et al: "Studies on Seed Treatment with Phoxim in White Grub Control" Abstract, vol. 19, No. 2, 1976, pp. 157-166 (ISSN: 0454-6296).
Igrc Barcic Jasminka et al: "Investigation of the Insecticide Seed Dressing on the Sugar Beet" Abstract, vol. 65, No. 2, Jul. 2000, pp. 89-97 (ISSN: 1331-7768).
Kataria H.R. et al: "Interactions of Fungicide and Insecticide Combinations against Rhizoctonia Damping-off and Root Rot in Canola" Abstract, vol. 123, No. 2, 1993, pp. 233-246 (ISSN: 0003-4746).

* cited by examiner

Primary Examiner — James H. Alstrum-Acevedo
(74) Attorney, Agent, or Firm — Brian D. McAlhaney

(57) ABSTRACT

Method of protecting a germinating seed treated with a pesticide comprising placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide.

9 Claims, No Drawings

METHOD OF APPLYING PESTICIDES

This application is a 371 of International Application No. PCT/EP2005/006208 filed Jun. 9, 2005, which claims priority to GB 0412974.8 filed Jun. 10, 2004, the contents of which are incorporated herein by reference.

The present invention relates to a method of protecting a germinating seed treated with a pesticide in agriculture and horticulture.

Methods for protecting plant seed against pests are well known in the field. Usually pesticides, for example insecticides or fungicides are applied alone or in combinations directly onto seeds during a seed treatment prior to sowing. Seed treatment is well-known in the art and comprises different methods, for example seed dressing, seed coating or seed pelleting.

In seed treatments pesticides are generally applied in relatively high doses to achieve adequate protection against the pest to be fought. It is well known in the art that, for example, high doses of some pesticides in seed treatment, when they exceed a certain threshold, can delay germination, hamper the growth vigor of the plant or induce other negative effects during germination. These effects, that occur predominantly in the seedling stage of a plant, are collectively called "phytotoxic" effects. Examples of pesticides that may cause phytotoxic effects depending on dosing, way of application, environmental conditions and similar parameters, can be found amongst the systemic insecticides, such as, for example, imidacloprid, thiamethoxam and clothianidin. Said phytotoxic effects are an economic disadvantage and restrict the flexibility of the corresponding pesticide in seed treatment. One way to avoid said phytotoxic effects is suggested in WO 01/13722 where it is proposed to apply the pesticide on a separate particle and place one of these pesticide-containing particles next to a seed. WO 01/13722 describes this method for pelleted lettuce seeds in combination with pellets containing the insecticide imidacloprid.

When the method as described in WO 01/13722 is applied in the plant-producing industry there still exist some economical disadvantages. Although modern seed sowing machines are quite accurate, a sowing failure of 1 to 2% can be present. Therefore, considering the mass-cultivation of plants that is characteristic for this industry, a significant portion of plants will receive no pesticide protection at all due to a sowing failure of the pesticide-containing particle during sowing.

A further important industry in the art of the invention is that of young plant growers. Young plant growers cultivate high-value plants, such as, for example lettuce, brassica, pepper, tomato and melon, in nurseries from the point in time of sowing the seed until the plant reaches the young plant stage. Typically, the young plant stage is reached between 4 and 6 weeks after sowing of the seed. Then the young plants are usually sold to a customer, who then transplants the young plants into an open-land field for further cultivation. Generally, while being in the nurseries of the young plant growers, the plants are cultivated on plant trays. Besides the already mentioned loss of pesticide-containing particles due to sowing failures, pesticide-containing particles can also be lost, for example during transport of said plant trays or during said transplanting into the open-land field.

By applying the method as described in WO 01/13722 in those high-value plant growing industries there is a significant financial loss as a considerable portion of plants will receive no pesticide protection at all due to sowing failures or due to loss of pesticide-containing particles during said plant handling operations.

The present invention recognizes the need to increase the yield of suitably pesticide-protected plants in mass-cultivations, that start already at the seed stage, without investments into the improvement of labour intensive operations, such as, for example, sowing or transplanting.

Typically, the plant trays used by the young plant growers contain a multitude of individual plant containers. Depending on the application, the size of said plant containers is in the range of 1×1 cm to 4×4 cm. The seed and the pesticide-containing particle are placed individually into the plant containers. Therefore, due to automation with the use of sowing machines, the seed and the pesticide-containing particle can easily have a distance to each other of up to 4 cm in the individual plant containers. Usually, the plants are cultivated for 4 to 6 weeks in the plant trays before they reach the young plant stage and are then transplanted into the open-land field. For a seed where a considerable distance, such as, for example 4 cm, lies between the seed and its corresponding pesticide-containing particle it is questionable, that the plant germinating from that seed receives an adequate pesticide protection already early after transplanting, because the pesticide has to be transported over that distance solely by diffusion.

The present invention also recognizes the need of conveying an early pesticide protection to those transplanted plants, where the seed and its corresponding pesticide-containing particle were situated in a considerable distance in the plant container.

The problems of increasing the yield of suitably pesticide protected plants in mass-cultivations and of conveying an early pesticide protection to transplanted plants are both overcome by the instant invention.

According to the instant invention it is suggested not to apply the Effective Dose of the pesticide, that is a dose that is sufficient to protect one seed germ, on the pesticide-containing particles, which are placed next to the seed to be protected, but to distribute the Effective Dose between the seed and the pesticide-containing particles in a suitable ratio.

The invention relates to a method of protecting a germinating seed treated with a pesticide comprising placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. This guarantees that those plants, that did not receive or have lost their pesticide-containing particles do not remain unprotected, as the pesticide will always be present directly on the seed at a dose that is lower than or equal to the Maximal Non-Phytotoxic Dose of the pesticide. By using said method a basic level of pesticide protection is conferred to all plants in a mass-cultivation without causing undesirable phytotoxic effects during germination. Said basic level of pesticide protection will also be present immediately after transplanting, even with those plants, whose pesticide-containing particles were situated in a considerable distance from the seed in the plant container. Thus an early protection is conferred to those plants without causing undesirable phytotoxic effects during germination.

Within the context of the present invention certain terms are meant to have a specific meaning as defined below:

According to the instant invention an "Effective Dose" is a dose of a pesticide in a seed treatment that is giving sufficient control of the pest under normal test conditions. Usually, said sufficient control is equal to the maximal obtainable control of the pest for the pesticide under normal test conditions. Said normal test conditions generally reflect the natural environment where the plants are to be grown and where the pest is to be fought. "Sufficient control of the pest" represents an economically interesting pest control and is, as a rule, in a range of between 70-100% control.

Tests for pesticidal activity of pesticides in seed treatments are well known in the art and include, for example, tests for insecticidal, fungicidal or miticidal activities. Examples for said tests can be found in Jukes et al. (in: "Evaluation of non-organophosphorus insecticides for controlling the cabbage root fly. The insecticide conundrum", Proceedings 52nd International Symposium on Crop Protection, Gent, Belgium, 2000), Ester et al. (in: "Filmcoating the seed of cabbage (*Brassica oleracea* L. covar. *Capitata* L.) and cauliflower (*Brassica oleracea* L. var. *Botrytis* L.) with imidacloprid and spinosad to control insect pests", 2003, Crop Protection 22(5): 761-768), Ester and Brantjes (in: "Pelleting the seed of iceberg lettuce (*Lactuca sativa* L.) and butterhead lettuce (*Lactuca sativa* L. var. *capitata* L.) with imidacloprid to control aphids", Proceedings 50th International Symposium on Crop Protection, Gent, Belgium, 1998) and Hofer et al. (in: "Thiamethoxam (CGA 293'343)—a novel insecticide for seed delivered insect control", 2001 BCPC Symposium Proceedings No. 76, Seed Treatment). Information about Effective Doses for individual pesticides to be used in specific plant/pest systems are required by the regulatory authorities and are thus routinely determined in the art for regulatory purposes. Examples for such Effective Doses are: 0.8 g of imidacloprid per 1000 lettuce seeds (dutch registration code no. 11455), 0.096 g of chlorpyriphos per 1000 brassica seeds (dutch registration code no. 10968), 0.175 g of metalaxyl-m per kg brassica seeds (dutch registration code no. 12280), 1 g of carbendazim per kg onion seeds (dutch registration code no. 8672), 5 g of iprodioneper kg carrot seeds (dutch registration code no. 8928) and 1.6 g of thiramper kg radish seeds (dutch registration code no. 11492).

The methodology to determine pesticidal activity including the Effective Dose are known in the art and are described, for example, in the above-mentioned references. In general, the Effective Dose can range from 0.0001 to 1000 g of pesticide per kg seeds. However, the specific value of the Effective Dose may depend on a variety of parameters such as, for example, physical and biological factors which are unique for each individual pesticide (stability of the compound in the test environment, efficacy against the pest to be controlled) and the nature of the plant material to be protected (surface area, consistency, moisture content and similar parameters). It may also vary depending on different pesticide formulations and methods of pesticide application for the same plant/pest system.

According to the instant invention a "Maximal Non-Phytotoxic Dose" is that proportion of the Effective Dose that is just sufficiently low not to cause an economically undesirable phytotoxic effect on the plant. Examples for phytotoxic effects are a delay in germination, a hampering of the growth vigor of the plant and other negative effects during germination. Tests for phytotoxic effects in seed treatments are well known in the art and include, for example the analysis of the germination percentage, the analysis of the germination speed, the analysis of the yield of normal developed plants and the analysis of the plant leaf area development. An example for said tests can be found in WO 01/13722.

As a rule, an economically undesirable phytotoxic effect is seen, when the value of a beneficial parameter, such as, for example, the germination rate or the growth of the size of the plant leaf area, is diminished below 95-75% of the value of the untreated control. Here the economical significance of the parameter chosen for the phytotoxicity test has to be taken into account. Whereas a 25% decrease of a parameter with medium economical significance, such as the size of the plant leaf area, is economically acceptable, a 5% decrease of a parameter with high economical significance, such as the germination percentage, which dictates the number of marketable plants, is the maximum acceptable. It has to be mentioned that for some rare and exceptional plant/pest/pesticide systems a certain amount of phytotoxicity exceeding the above mentioned values might be tolerated economically as an increased pesticide protection available directly to the seed would compensate the economic disadvantage caused by the phytotoxic effect. The invention is also meant to cover these rare and exceptional cases.

Information about Maximal Non-Phytotoxic Doses for pesticides for individual plant species are required by the regulatory authorities and are thus routinely determined in the art for regulatory purposes. Methods for determining Maximal Non-Phytotoxic Doses of plant pesticides are thus well known to the skilled artisan and are described, for example, in the above-mentioned reference. The methodology to determine Maximal Non-Phytotoxic Doses of plant pesticides are known in the art. In general, Maximal Non-Phytotoxic Doses can range from 0.0001 to 1000 g of pesticide per kg seeds. However, the specific value of the Maximal Non-Phytotoxic Dose may depend on a variety of parameters such as, for example, physical and biological factors which are unique for each individual pesticide (stability of the compound in the test environment, phytotoxicity against the plant species) and the nature of the plant material to be protected (surface area, consistency, moisture content and similar parameters). It may also vary depending on different pesticide formulations and methods of pesticide application for the same plant species.

According to the instant invention in the expression "placing pesticide-containing particles next to the pesticide-treated seed", and the expression "next to the pesticide-treated seed" means sufficiently close to a locus of the pesticide-treated seed to allow diffusion of the pesticide from the pesticide-containing particles to the locus of the pesticide-treated seed.

It has to be mentioned, that the pesticide-containing particles can be placed before, during or after the sowing of the pesticide-treated seed, the invention is meant to cover all these embodiments of the invention.

According to a specific embodiment of the invention in the expression "placing pesticide-containing particles next to the pesticide-treated seed" and the expression "next to the pesticide-treated seed" means in a distance of less that 10 cm, preferably less than 5 cm, more preferably less 4 cm, most preferably less than 1 cm, to a locus of the pesticide-treated seed.

In particular it is also envisaged that pesticide-containing particles are placed (planted or sown) into an open-land field at the time a young plant is transplanted from a nursery tray into an open land, irrespective of (i) whether pesticide-containing particles are also placed in the nursery tray with the then pesticide-treated seeds or (ii) whether the pesticide on the pesticide-containing particles is the same or different from the pesticide-containing particles, if present, or pesticide-treated seeds in the nursery tray. The placing of the pesticide-containing particles in the open-land field is such that to allow diffusion of the pesticide from the pesticide-containing particles to the locus of the young plant. Such as a method allows a second level of pesticide protection to the transplanted young plant with the same, or a different, pesticide. This can be advantageous especially when pesticide protection is sought against pests that are not known to damage the young plant in the nursery trays, but only in the open-land field.

In a preferred embodiment of the invention it is envisaged that the pesticide dose contained in the pesticide-treated seed is more than or equal to the Minimal Pesticidal Dose of the pesticide and less then or equal to the Maximal Non-Phytotoxic Dose of the pesticide. According to the instant invention a "Minimal Pesticidal Dose" is a dose of a pesticide in a seed treatment that is needed to provide a partial control of the pest under normal test conditions, wherein said normal test conditions are as described above. "Partial control of the pest" means a measurable pest control under normal test conditions and is lower than said "sufficient control of the pest", which is described above.

In an especially preferred embodiment of the invention it is envisaged that the pesticide dose contained in the pesticide-treated seed is equal to the Maximal Non-Phytotoxic Dose of the pesticide. Thus a high level of protection is conferred directly to the plant and simultaneously the economic disadvantage due to phytotoxicity in the young plant stage is kept at an economically acceptable level.

In another embodiment of the invention, the pesticide dose contained in the pesticide-treated seed is in a range of between 10, 20, 30, 40, 50, 60, 70, 80 and/or 90% of the Effective Dose, with any individual number falling with this range of between 10% and 90% and including the boundaries of the range, 10% and 90%, also being part of the invention. Consequently, the respective dose that is applied to the pesticide-containing particles is in a range of between 90, 80, 70, 60, 50, 40, 30, 20 and/or 10% of Effective Dose, with any individual number falling with this range of between 10% and 90% and including the boundaries of the range, 10% and 90%, also being part of the invention. The total dose that is applied to the seed and the pesticide-containing particles adds up to 100%, corresponding to the Effective Dose. If, therefore, for example, the dose applied to the seed is 10% of the Effective Dose, the pesticide-containing particles receive the remaining 90% of the Effective Dose. The maximal dose that is applied to the seed to be protected may vary considerably within the above given range of between 10% to 90% of the Effective Dose depending on the plant species to be treated and the pesticide to be used, respectively. Other parameters which may also be considered in the proper dosing of the pesticide are, for example, humidity, temperature, soil conditions and similar parameters.

Seed treatment methods are well known in the art, and they may be used readily to apply the pesticide to the seed. Examples for seed treatment methods are shown in Butler (in: "Coatings, films and treatments", Seed World, Oct. 19-24, 1993), Callan (1975, Outlook on Agriculture 8: 271-274), Maude (in: "Vegetable seed treatments", Seed Treatment, CIPAC Monograph 2, Jeffs, Ed., pages 91-101, 1978), U.S. Pat. Nos. 5,876,739 and 2,502,809.

The pesticide formulation and methods of treating seeds therewith are known in the art. Generally, the pesticide can be formulated, for example as a powder, as a wettable powder, as a water soluble powder, as a liquid formulation (e.g. aqueous or solvent-based), including a flowable concentrate (such as a suspension concentrate), solution and capsule suspension. The formulation of the pesticide may also include an agent for assisting the adhesion of the formulation to the seed, for example a mineral oil or a film-forming barrier. The pesticide or the formulation may be applied to the seed as a dust, as a slurry, as a soak, as a film-coating or as an encapsulation. The method of application depends on the chemical and physical properties of the seed surface and the pesticide itself and may be varied. The invention is intended to include any technique which is to be used.

A coating may be added to the seed using conventional coating or pelleting techniques, multiple different coatings are possible. The coating may comprise any conventional material commonly used in the art for protecting or pelleting seed. Suitable materials include clays, such as sub-bentonite and bentonite, vermiculite, along with additives such as perlite, pumice, metal stearates, polyethylene, polystyrene, polyurethane, talcum powder, polypropylene, polyvinyl chloride, starches, loams, sugars, Arabic gums, organic polymers, celluloses, flours such as wood flours, quartz powders and the like. The coating may comprise the pesticide, but may also comprise further adjuvants, for example pigments, antioxidants, dyes, odorants, agents, that convey a bitter taste, or beneficial substances for the plant, for example one or more other pesticides, such as, for example, an acaricide, bactericide, fungicide, insecticide, molluscicide, nematicide or rodenticide, one or more herbicides, growth hormones, nutrients, fertilizers, for example nitrogen-, potassium- or phosphorus-containing fertilizers, germination stimulants, micro organisms, pheromones or biological preparations.

In a specific embodiment of the invention the seed is used in the form of a seed-containing pellet. A seed-containing pellet is formed with a filler material surrounding the seed. Many diverse filler materials are known in the art and include, among others, peat, soil, calcium carbonate, dolomite, gypsum, clay minerals, phosphates, titanium dioxide, humus and activated charcoal. Any agriculturally suitable material can be employed. An adhesive material is often included in such a seed-containing pellet to ensure that the filler material remains in contact with the seed. Many acceptable adhesives are known in the art and include, among others, synthetic glues, vegetable glues, gelatin and sugars. A coating may be applied before or after the pelleting process.

According to the invention a "pesticide-containing particle" refers to a composition comprising a pesticide and a suitable inert carrier. Suitable examples of "pesticide-containing particle" are pesticide-containing pellets and pesticide-containing granules. Pesticide-containing particles are well known in the art, for example see WO 01/13722, DE-4343176-A1 and CA Patent 1-143-651. The type of pesticide-containing particles chosen will depend upon the particular purpose envisaged and the physical, chemical and biological properties of the pesticide.

It is preferred that the pesticide-containing particles comprises, by weight, 0.0001 to 95%, more preferably 1 to 85%, for example 5 to 60%, of the pesticide.

The pesticide-containing particles may have a core. The core may be inert, for example, a glass-bead, perlite, plastic, pumice or any other suitable material. If desired however, it is also possible to use non-germinating seed, which is for example inactivated by heat treatment, gamma rays or microwaves, or other biodegradable organic material.

The pesticide-containing particles may contain a filler material. The filler material can be applied to the particles before or after applying the pesticide. All types of filler material commonly used in seed treatment can be used. The types of filler materials are described above.

In an embodiment of the invention a substance is incorporated into the pesticide-containing particle to regulate the release of the pesticide, for example, after a certain time or at under certain conditions, such as temperature, moisture and humidity. Such substances are known in the art. Such a controlled release is advantageous when pest protection is not needed immediately on sowing or planting the seed.

The pesticide-containing particles may comprise further adjuvants such as pigments, antioxidants, dyes, odorants, agents, that convey a bitter taste, or beneficial substances for the plant, for example one or more other pesticides, for example acaricides, bactericides, fungicides, insecticides, molluscicides, nematicides or rodenticides, herbicides, growth hormones, nutrients, fertilizers, for example nitrogen-, potassium- or phosphorus-containing fertilizers, germination stimulants, micro organisms, pheromones or biological preparations.

The pesticide-containing particles may be produced in any desired shape and size that allows for precise placement next to the pesticide-treated seed or transplanted young plant.

According to a preferred embodiment of the invention, the pesticide-containing particles have substantially the same size, shape and weight as the seed. It is thus possible with precision sowing machinery to place a precisely defined number (as determined by the grower based on pest pressure) of pesticide-containing particles per plant next to the seed. Thus in a simple way both sub- and overdose can be effectively avoided.

According to a further preferred embodiment of the invention one to four, especially one, pesticide-containing particle is used per pesticide-treated seed. The ratio also applies in the event the pesticide-containing particles are used in the open-land field with transplanted young plants. Thus automated sowing can be carried out in the most cost-effective way. Machinery for use in such methods exist, and if desired can be adapted for a specific ratio.

According to a further preferred embodiment of the invention, both pesticide-containing particles and pesticide-treated seeds have a substantially uniform diameter ranging from 0.5 to 5 millimeter.

The seeds may be from the following useful plants: cereals, for example wheat, barley, rye, oats, rice, maize or sorghum; beet, for example sugar or fodder beet; fruit, for example pome fruit, stone fruit and soft fruit, for example apples, pears, plums, peaches, almonds, cherries or berries, for example strawberries, raspberries and blackberries; legumes, for example beans, lentils, peas or soya beans, oil crops, for example oilseed rape, mustard, poppies, olives, sunflowers, coconut, castor-oil plants, cacao or peanuts; cucurbits, for example pumpkins, cucumbers or melons; fibre plants, for example cotton, flax, hemp or jute; citrus fruit, for example oranges, lemons, grapefruit or mandarins; vegetables, for example spinach, lettuce, asparagus, brassica (e.g. cabbage, broccoli, and cauliflower), carrots, onions, tomatoes, potatoes or capsicums; Lauraceae, for example avocado, Cinnamonium or camphor; or tobacco, nuts, coffee, egg plants, sugar cane, tea, pepper, grapevines, hops, Musaceae, latex plants or ornamentals (such as houseplants used in outdoor gardening or landscaping).

The seeds may be preferably from the following useful plants: beet, for example sugar or fodder beet; vegetables, for example spinach, lettuce, asparagus, brassica, carrots, onions, tomatoes, cucurbits, potatoes or capsicums; tobacco.

The seeds may be most preferably from vegetables, for example lettuce, brassica, tomatoes and cucurbits.

The method according to the instant invention can be used to protect useful plants against pests, for example insects, representatives of the order Acarina, molluscs, nematodes, microorganisms, for example phytopathogenic fungi, or rodents.

The method according to the instant invention can be used preferably to protect useful plants against insects, representatives of the order Acarina or nematodes. Examples of insects are:

of the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Astylus atromaculatus*, *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Elasmopalpus* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Heteronychus arator*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

of the order Coleoptera, for example, *Agriotes* spp., *Anthonomus* spp., *Atomaria linearis*, *Chaetocnema tibialis*, *Conotrachelus* spp., *Cosmopolites* spp., *Curculio* spp., *Dermestes* spp., *Diabrotica* spp., *Dilopoderus* spp., *Epilachna* spp., *Eremnus* spp., *Heteronychus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psyliodes* spp., *Rhizopertha* spp., *Scarabeidae*, *Somaticus* spp., *Sitophilus* spp., *Sitotroga* spp., *Tanymecus* spp., *Tenebrio* spp., *Tribolium* spp., *Trogoderma* spp. and *Zabrus* spp.;

of the order Orthoptera, for example, *Blatta* spp., *Blattella* spp., *Gryllotalpa* spp., *Leucophaea maderae*, *Locusta* spp., *Periplaneta* spp. and *Schistocerca* spp.;

of the order Psocoptera, for example *Liposcelis* spp.;

of the order Anoplura, for example, *Haematopinus* spp., *Linognathus* spp., *Pediculus* spp., *Pemphigus* spp. und *Phylloxera* spp.;

of the order Isoptera, for example, *Reticulitermes* spp.;

of the order Mallophaga, for example, *Damalinea* spp. and *Trichodectes* spp.;

of the order Thysanoptera, for example, *Frankliniella* spp., *Hercinothrips* spp., *Taeniothrips* spp., *Thrips palmi*, *Thrips tabaci* and *Scirtothrips aurantii*;

of the order Heteroptera, for example, *Cimex* spp., *Distantiella theobroma*, *Dysdercus* spp., *Euchistus* spp. *Eurygaster* spp. *Leptocorisa* spp., *Nezara* spp., *Piesma* spp., *Rhodnius* spp., *Sahlbergella singularis*, *Scotinophara* spp. and *Triatoma* spp.;

of the order Homoptera, for example, *Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*;

of the order Hymenoptera, for example, *Acromyrmex*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.;

of the order Diptera, for example, *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella* frit, *Pegomyia hyoscyami, Phorbia* spp., *Rhagoletis pomonella, Sciara* spp., *Stomoxys* spp., *Tabanus* spp., *Tannia* spp. and *Tipula* spp.;

of the order Siphonaptera, for example, *Ceratophyllus* spp. and *Xenopsylla cheopis*; or of the order Thysanura, for example, *Lepisma saccharina*.

Amongst the representatives of the order Acarina, for example, *Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.

Amongst nematodes, for example root knot nematodes, stem eelworms and foliar nematodes; especially *Heterodera* spp., for example *Heterodera schachtii, Heterodora avenae* and *Heterodora trifolii; Globodera* spp., for example *Globodera rostochiensis; Meloidogyne* spp., for example *Meloidogyne incoginita* and *Meloidogyne javanica; Radopholus* spp., for example *Radopholus similis; Pratylenchus*, for example *Pratylenchus neglectans* and *Pratylenchus penetrans; Tylenchulus*, for example *Tylenchulus semipenetrans; Longidorus, Trichodorus, Xiphinema, Ditylenchus, Aphelenchoides* and *Anguina*.

And amongst crucifer flea beetles (*Phyllotreta* spp.), root maggots (*Delia* spp.) and cabbage seedpod weevil (*Ceutorhynchus* spp.).

The pesticide-containing particles and pesticide-treated seeds may have the same pesticide or different. Further, the pesticide on the particles or seeds may be more than one pesticide or active ingredient, which can be of different types of pesticides (e.g. fungicide, insecticide, acaricide, nematicide). In an embodiment, the pesticide-containing particle has one or more fungicide and one or more insecticide mixture of active ingredients. Alternatively, the pesticide-containing particle has one or more types of insecticide, such as thiamethoxam, imidacloprid and tefluthrin.

Generally, the difficulties, such as phytotoxicity and physical impracticabilities, with including several different pesticides onto a seed prohibit the use of several pesticides at a rate effective for pest control. Accordingly, a particular advantage of the present invention is that several pesticides can be available to protect the seed and young plant at a vulnerable stage of its growth through the use of a defined number of pesticide-containing particles per pesticide-treated seed or transplanted young plant.

The pesticide is, for example, an acaricide, a bactericide, a fungicide, an insecticide, a molluscicide, a nematicide or a rodenticide, or a mixture of two or more thereof, for example, a fungicide and an insecticide or two insecticides.

In an embodiment of the invention, the pesticide is an acaricide, a fungicide, nematicide or an insecticide, or a mixture of two or more thereof, for example, a fungicide and an insecticide or two insecticides.

It is preferred that more than one pesticide, whether of the same type or different type, are present on a seed and/or particle.

According to another embodiment of the invention, the pesticide is an acaricide or an insecticide, such as, for example, spinosad, chlorpyriphos, imidacloprid, benfuracarb, clothianidin, fipronil, chlorfenvinphos and thiamethoxam, or a mixture of two or more thereof.

According to an especially preferred embodiment of the invention, the pesticide is at least one of imidacloprid, thiamethoxam, clothianidin or abamectin.

In an embodiment, the pesticide-containing particles contain the same pesticide as the pesticide-treated seeds.

In another embodiment, the pesticide-containing particles contain a different pesticide from the pesticide-treated seeds, which can be a different type of pesticide or a different active ingredient within the same type of pesticide. Preferably, the pesticide on the seed is at least thiamethoxam, azoxystrobin, fludioxonil and metalaxyl-M and the pesticide on the particle is at least abamectin.

A further aspect of the invention relates to a method of producing plants comprising placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide.

A further aspect of the invention relates to plants produced by a method comprising placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide.

The invention claimed is:

1. A method of protecting a germinating seed comprising:
    placing, individually and next to one another, a germinating seed and a set of one to four non-germinating seeds, wherein said set of non-germinating seed are treated with one or more pesticides selected from acaricides, bactericides, fungicides, insecticides, mollusicides, and rodenticides and said germinating seed is treated with one or more pesticides selected from acaricides, bactericides, fungicides, insecticides, mollusicides, and rodenticides, wherein said set of non-germinating seed and germinating seed are treated independently of one another and wherein the amount of pesticide is such that the germinating seed and the set of non-germinating seed together contain an effective dose of the one or more pesticides.

2. The method according to claim 1, wherein the pesticide contained in the geminating seed is in a range of between 10 and 90% of the effective dose and the respective dose that is contained in the set of non-germinating seed is in a range of between 90 and 10% of the effective dose.

3. The method according to claim 1, wherein the germinating seed is used in the form of a seed-containing pellet.

4. The method according to claim 1, wherein the set of non-germinating seeds have substantially the same size, shape and weight as the germinating seed.

5. The method according to claim 1, wherein one non-germinating seed is placed next to the germinating seed.

6. The method according to claim 1, wherein the one or more pesticides is an acaricide or an insecticide or a mixture of two or more thereof.

7. The method according to claim 6, wherein the pesticide is imidacloprid or thiamethoxam.

8. The method according to claim 1 wherein a different pesticide is applied to said germinating seed and said set of non-germinating seed.

9. A method of producing plants comprising sowing, individually and next to one another, a germinating seed and a set of one to four non-germinating seeds, wherein said set of non-germinating seed are treated with one or more pesticides selected from acaricides, bactericides, fungicides, insecticides, mollusicides, and rodenticides and said germinating seed is treated with one or more pesticides selected from acaricides, bactericides, fungicides, insecticides, mollusicides, and rodenticides, wherein said set of non-germinating seed and germinating seed are treated independently of one another and, wherein the amount of pesticide is such that the germinating seed and the set of non-germinating seed together contain an effective dose of the one or more pesticides.

* * * * *